United States Patent
Case et al.

(10) Patent No.: US 10,172,996 B2
(45) Date of Patent: Jan. 8, 2019

(54) MEDICAL SOLUTION AUTHENTICATION

(71) Applicant: Fenwal, Inc., Lake Zurich, IL (US)

(72) Inventors: Brian C. Case, Lake Villa, IL (US); Steven R. Katz, Deerfield, IL (US)

(*) Notice: Subject to any disclaimer, the term of this patent is extended or adjusted under 35 U.S.C. 154(b) by 237 days.

(21) Appl. No.: 14/832,849

(22) Filed: Aug. 21, 2015

(65) Prior Publication Data

US 2016/0051746 A1 Feb. 25, 2016

Related U.S. Application Data

(60) Provisional application No. 62/040,660, filed on Aug. 22, 2014.

(51) Int. Cl.
  *A61M 1/02* (2006.01)
  *A61M 1/26* (2006.01)
  (Continued)

(52) U.S. Cl.
  CPC .......... *A61M 1/3696* (2014.02); *A61M 1/265* (2014.02); *A61M 1/342* (2013.01);
  (Continued)

(58) Field of Classification Search
  CPC ...... A61M 1/02; A61M 1/024; A61M 1/0259; A61M 1/265; A61M 1/30; A61M 1/301; A61M 1/34; A61M 1/342; A61M 1/3455; A61M 1/3496; A61M 1/36; A61M 1/3672; A61M 1/3696; A61M 2205/60; A61M 2205/6018; A61M 2205/502; A61M 2205/3584; A61M 2205/6063; A61M 2205/6072; A61M 2205/18; A61M 2205/52; A61M 2202/0474; A61M 2202/0413; B01D 61/24; B01D 61/30; B01D 61/32; G06F 19/34; G06F 19/3406; G06F 19/3412; G06F 19/3418; G06F 19/3456; G06F 17/30386
  (Continued)

(56) References Cited

U.S. PATENT DOCUMENTS

| | | |
|---|---|---|
| 5,286,959 A | 2/1994 | Demachi |
| 7,753,085 B2 * | 7/2010 | Tribble ................... B65B 3/003 |
| | | 141/104 |

(Continued)

*Primary Examiner* — Joseph W Drodge
(74) *Attorney, Agent, or Firm* — Hanna Yoon; Scott M. Day

(57) ABSTRACT

A system of authenticating a medical solution used in a blood processing procedure, comprising a blood processing system having a user interface and access to a database of medical solutions identifiable by identifiers, wherein the blood processing system guides a user through steps of the procedure and the user interface prompts the user to execute an action as part of a step; a fluid circuit having an inlet for a medical solution, wherein the fluid circuit is coupled to the fluid processing system; wherein a step of the blood processing procedure comprises drawing a solution into the circuit, wherein the interface receives a user input of an identifier of the solution prior to the fluid processing system executing the step; wherein the fluid processing system is configured to compare the received identifier to medical solution identifiers within the database and, based on a result of the comparison, executing the step.

21 Claims, 4 Drawing Sheets

(51) Int. Cl.
*A61M 1/34* (2006.01)
*A61M 1/36* (2006.01)
*G06F 17/30* (2006.01)
*G16H 40/63* (2018.01)
*G06F 19/00* (2018.01)

(52) U.S. Cl.
CPC ........ *A61M 1/3455* (2013.01); *A61M 1/3672* (2013.01); *G06F 17/30386* (2013.01); *G06F 19/00* (2013.01); *G16H 40/63* (2018.01); *A61M 2202/0413* (2013.01); *A61M 2202/0474* (2013.01); *A61M 2205/18* (2013.01); *A61M 2205/3584* (2013.01); *A61M 2205/502* (2013.01); *A61M 2205/52* (2013.01); *A61M 2205/60* (2013.01); *A61M 2205/6018* (2013.01); *A61M 2205/6072* (2013.01)

(58) Field of Classification Search
USPC ...... 210/645, 646, 91, 143, 321.6; 604/4.01, 604/5.01, 6.01, 19, 30, 65, 67, 93.01, 604/189, 403, 404
See application file for complete search history.

(56) References Cited

U.S. PATENT DOCUMENTS

| | | | |
|---|---|---|---|
| 7,927,313 B2 | 4/2011 | Stewart et al. | |
| 8,032,397 B2* | 10/2011 | Lawless | G06F 19/3418 705/2 |
| 8,291,337 B2* | 10/2012 | Gannin | A61M 5/172 604/131 |
| 8,676,600 B2* | 3/2014 | Case | G06Q 10/087 705/2 |
| 8,685,258 B2* | 4/2014 | Nguyen | A61K 35/16 210/782 |
| 9,671,349 B2* | 6/2017 | Schoonover | G01N 21/84 |
| 2002/0173875 A1* | 11/2002 | Wallace | G06F 19/322 700/242 |
| 2003/0074223 A1* | 4/2003 | Hickle | A61J 1/14 705/2 |
| 2003/0154108 A1* | 8/2003 | Fletcher-Haynes | G16H 10/40 705/3 |
| 2004/0172169 A1* | 9/2004 | Wright, IV | A61J 3/074 700/265 |
| 2005/0210834 A1* | 9/2005 | Kamineni | A61J 1/20 53/415 |
| 2006/0026205 A1* | 2/2006 | Butterfield | G06F 19/3406 |
| 2006/0047538 A1* | 3/2006 | Condurso | G06F 19/326 705/3 |
| 2009/0217202 A1* | 8/2009 | Foley | A61M 1/3693 715/810 |
| 2010/0282834 A1* | 11/2010 | Devergne | A61M 1/16 235/375 |
| 2012/0038651 A1* | 2/2012 | Case | G06Q 10/087 345/440 |
| 2012/0041778 A1* | 2/2012 | Kraft | B65D 51/2828 705/2 |
| 2012/0315231 A1* | 12/2012 | Lin | A61K 8/342 424/61 |
| 2013/0138452 A1* | 5/2013 | Cork | G06Q 10/087 705/2 |
| 2013/0334139 A1* | 12/2013 | Blickhan | A61M 1/0272 210/650 |
| 2014/0045671 A1 | 2/2014 | Min et al. | |
| 2014/0350450 A1* | 11/2014 | Case | G06F 19/322 604/6.01 |
| 2015/0355789 A1* | 12/2015 | O'Mahony | G06F 19/3406 715/810 |
| 2015/0355790 A1* | 12/2015 | O'Mahony | G06F 19/3406 715/771 |

* cited by examiner

MEDICAL SOLUTION AUTHENTICATION

FIELD OF THE DISCLOSURE

The present disclosure generally relates to an authentication system for authenticating medical solution containers. More particularly, the present disclosure relates to an authentication system of solution containers used in apheresis or blood processing procedures.

BACKGROUND

Infusion solutions, blood additive solutions, blood component solutions, replacement fluids, and other medical solutions used in apheresis or blood processing procedures are contained in solution containers having closed-off access ports that maximize solution sterility until the container is opened at the time of use. Access ports of different solution containers and different manufacturers come in a variety of types that are accessed through corresponding access tools operated by a human operator. The various types of ports include membrane ports, which are ports that are sealed off by a membrane and punctured by a piercing tool such as a cannula or spike; luer-fitted ports, which are ports fitted with a female luer fitting and breached by a tool with a complementary male fitting; and other fitted ports, which are accessed by corresponding tools that mate with the structure of the port. Generally, an access tool is often part of a set or kit manufactured for a specific type of apheresis or blood processing procedure and is connected by tubing to an intended destination of the solution within the kit.

In some cases, two or more medical solution containers may be used simultaneously during apheresis or blood processing procedures. For example, various combinations of saline solution bags, anti-coagulant bags, RBC additive bags, platelet additive bags, and/or a variety of replacement fluids, such as albumin, RBCs, platelets, etc. may be used in a single apheresis or blood processing procedure. Although these solutions have very different functions and properties, the containers in which they are held are often quite similar in appearance, and it is up to the human operator to make sure that the correct access tool accesses the correct solution container.

SUMMARY

One embodiment relates to a blood processing system, comprising a blood processing device having a user interface and a memory. The system also comprises a database of medical solutions identifiable by identifiers and a fluid circuit for use with the blood processing device having an inlet for a medical solution. The blood processing device is configured to guide a user through one or more steps of a blood processing procedure including prompting a user to input an identifier of a medical solution, compare the identifier to information within the database, and authorize use of the medical solution upon verification of the identifier within the database.

Another embodiment relates to a blood processing system, comprising a blood processing device having a user interface and a memory, a database of medical solutions identifiable by identifiers, and a processing circuit. The processing circuit is configured to guide a user through one or more steps of a blood processing procedure including prompting the user via the user interface to execute one or more actions as part of a step, prompt the user via the user interface to input an identifier of a medical solution, receive the identifier of the medical solution via the user interface and identify the medical solution within the database based on the received identifier, and in response to identifying the medical solution within the database, proceeding with a step of the blood processing procedure.

Another embodiment relates to a blood processing system, comprising a blood processing device having a user interface and a memory, a database of medical solutions identifiable by identifiers, a medical solution port, and a processing circuit. The processing circuit is configured to provide a prompt to a user via the user interface as part of a multi-step blood processing procedure operated by the blood processing system. The processing circuit is also configured to receive an identifier of a medical solution from a user via the user interface before a step in the procedure, to determine whether the identifier is approved in the database for the step, and, based on the determination, to enable the blood processing system to perform the step of the procedure to process the medical solution via the medical solution port.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In some embodiments, solutions and kits of which the access tools are a part may not need to be procured from the same manufacturer.

In some embodiments, cross-access or improper intermixing or substitution of critically distinct fluids can be prevented.

In some embodiments, a practicable and low-cost manner for operators working with products from different manufacturers can be provided.

Some embodiments may allow for a standardized fail safe that could be implemented across multiple product lines and manufacturers.

Figure 1:
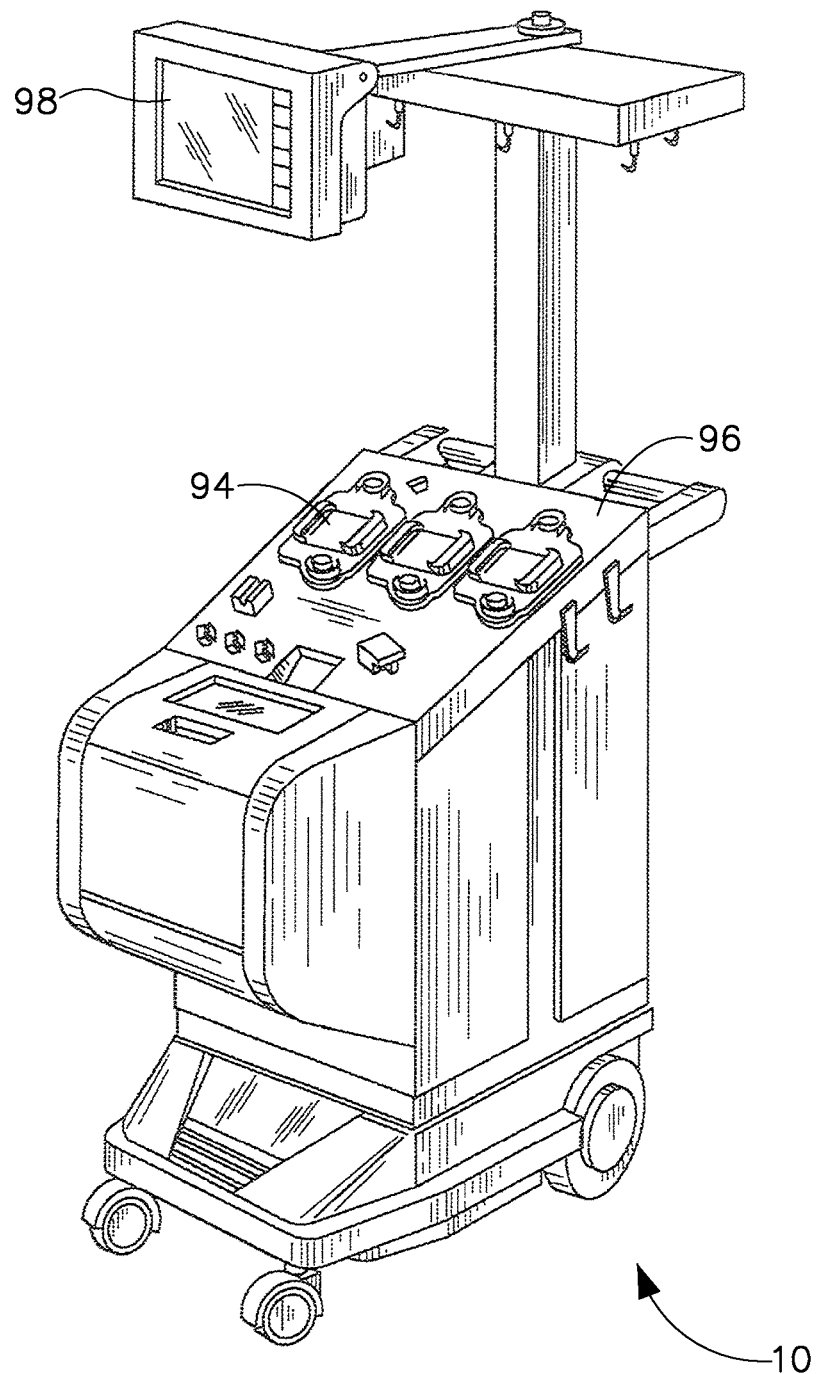
FIG. 1 is a perspective view of a fluid processing system, according to an exemplary embodiment.
Figure 2:
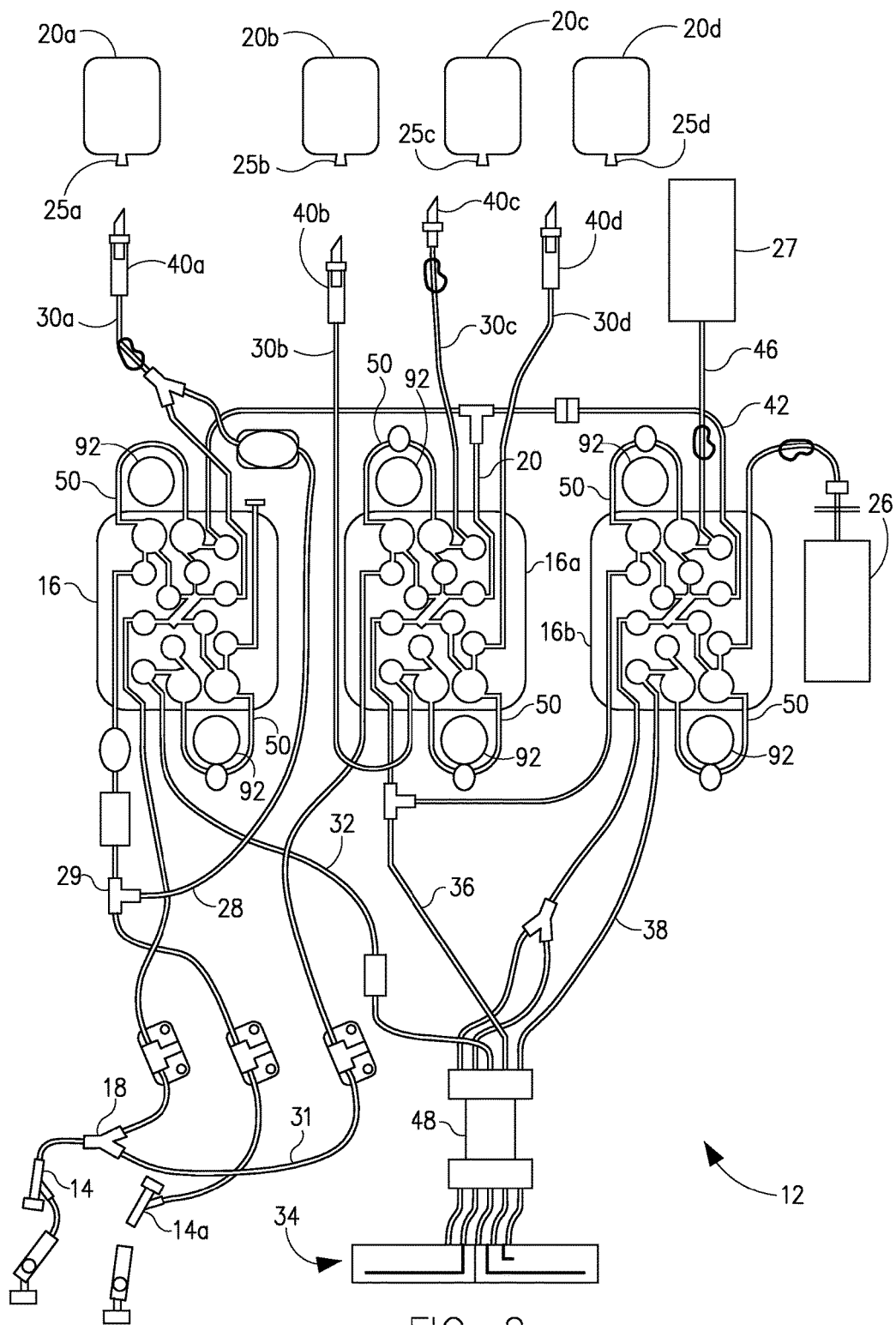
FIG. 2 depicts a single-use fluid circuit kit for an apheresis or blood processing procedure, according to an exemplary embodiment.

FIG. 1 depicts a generalized embodiment of a fluid processing system 10, which serves as an operation and connection center to various medical solution containers 20a-20d and a single-use fluid circuit kit 12 of FIG. 2 appropriate for a blood processing procedure, such as an apheresis procedure. The single-use fluid circuit kit 12 has tubings 30a-30d that are pre-connected to a plurality of cassettes 16, which are placed onto cassette holders 94 on a sloped front panel 96 of the fluid processing system 10 during operation of the blood processing procedure. An exemplary fluid processing system and fluid circuit kit are described in U.S. Patent Application Publication No. 2014/0045671, which is hereby incorporated by reference herein, although any suitable fluid processing system and fluid circuit kit may be used.

While described with reference to an apheresis system, the subject matter presented herein may be applied to other blood processing systems (e.g., dialysis machines, etc.) or other medical systems (e.g., internal or external infusion pumps, enteral feeding pumps, etc.). In some embodiments, the teachings herein could be used on any medical system that involves connecting a specific medical solution at a particular time or step within a multi-step procedure.

Referring to FIG. 1, the fluid processing system 10 may include a centrifuge or spinning membrane (not illustrated) used to separate blood components. The fluid processing system 10 may be programmed to separate blood into a variety of components (e.g., platelets, platelet-rich plasma, platelet-poor plasma, white cells, and red cells). Fluid procedures that may be processed include therapeutic plasma exchange procedures, RBC exchange procedures, and mononuclear cell collections, among many other blood processing procedures.

Referring to FIG. 2, the fluid circuit kit 12 contains a plurality of medical solution access tools 40a-40d that serve as inlets into the fluid circuit 12 for various medical solutions used in blood processing procedures, including but not limited to anticoagulant solutions, saline solutions, platelet additives, red cell additives, a variety of replacement fluids, etc. Medical solutions may comprise blood products or not comprise blood products. In alternative embodiments, medical solutions may comprise medicaments, nutrients, food, or other medical solutions. The medical solutions, which may or may not have been manufactured by the same entity as that of the fluid circuit 12, are contained in solution containers 20a-20d, each having a respective access port 25a-25d to which a respective access tool 40a-40d connects during the procedure. In turn, each access tool 40a-40d is connected to the plurality of cassettes 16 by a respective tubing 30a-30d that allows for each solution to reach its intended destination within the fluid circuit 12 for processing.

In one embodiment, the flow circuit 12 may be a "two needle" system, which includes a pair of blood source access devices 14 and 14a (e. g., phlebotomy needles) for fluidly connecting a blood source with the flow circuit 12. The blood source access devices 14 and 14a may be connected by tubing to a left cassette 16. One of the blood source access devices 14 may be used to draw blood from the blood source into the flow circuit 12 and is connected to the left cassette 16 by a y-connector 18. The other leg of the y-connector 18 is connected to tubing 31 which leads to a middle cassette 16a. The tubing 31 is connected, through the middle cassette 16a, to additional tubing 30c, which includes a container access tool 40c (e.g., a sharpened cannula or spike connector) for accessing the interior of a container 20c. During a blood processing procedure, a medical solution from the container 20c may be added to the blood from the blood source at the y-connector 18 prior to entering the left cassette 16.

The other blood source access device 14a may be used to deliver or return blood, a blood component, and/or some other medical solution to the blood source and is also connected to the left cassette 16 by a y-connector 29. The other leg of the y-connector 29 is connected to tubing 28 connected at its other end to a container access device 40a. The container access device 40a is associated with a container 20a having an amount of fluid (e.g., saline) that may be used to prime the flow circuit 12 and/or may be delivered to the blood source via the blood source access device 14a.

Additional tubing may be connected from one port of a cassette to another port of the same cassette, so as to form tubing loops 50 which interact with a fluid flow element or pump to flow fluid through the flow circuit 12.

As indicated, the fluid circuit 12 has a predetermined number of circuitries, and the fluid processing system 10 controls fluid flow according to pre-programmed settings ascribed to the specific blood processing procedure to be conducted. Therefore, it is desirable that the correct access tool 40a-40d connect to the correct solution container 20a-20d. A failsafe feature is thus included in this embodiment that prevents solution processing from proceeding any further if an incorrect solution container is connected at a particular processing step.

Figure 3:
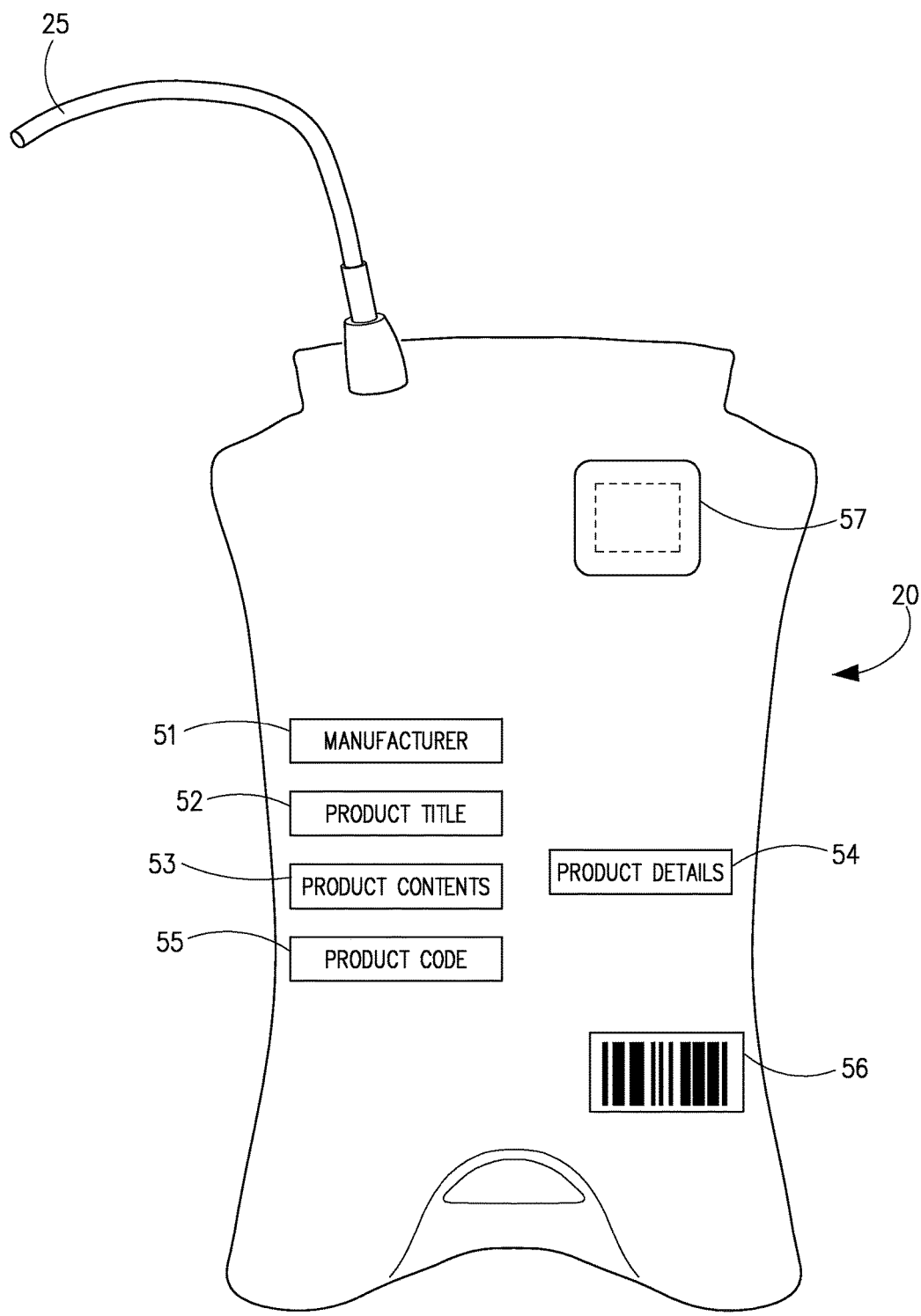
FIG. 3 is a perspective view of a medical solution container and its labeling components, according to an exemplary embodiment.

The failsafe feature of the fluid processing system 10 is based on recognition by the system 10 of each medical solution that it processes. Medical solution bags 20, regardless of specific manufacturer, generally have components listed in or referred to in their labeling. Referring to FIG. 3, these components may include manufacturer name 51, solution name 52, solution contents 53, content details 54, one or more product codes 55, a bar code 56, an active or passive RFID tag 57 for the product, and/or a photo-recognizable image, etc. The manufacturer name 51 may be a company name, trade name, etc. The solution name 52 may be a brand name or generic name. The solution contents 53 may include ingredients, composition state (e.g., emulsification), etc. The content details 54 may include details regarding any of the ingredients or details regarding any aspect of content (e.g., pH, osmolarity, temperature, tonicity, etc). Product code(s) 55 may be a manufacturer product code or a code designated by an end-user. Recognition by the system 10 of a medical solution may be achieved by the system 10 having access to a database containing one or more of the aforementioned components. The database may be located offline (i.e., not on a network) within the hard drive or memory of system 10 itself, or it may be located online on a network to which system 10 is linked. The fluid processing system 10 may contain a pre-populated medical solution database which is programmed into memory at the time of manufacturing of fluid processing system 10; or a database may be uploaded, manually entered by a user, or automatically entered (e.g., without requiring specific user input). The programming, upload, entry, or population of the database may occur at any time, such as prior to running a blood processing procedure, during the procedure, after running the procedure, etc.

Referring to FIG. 1, when a human operator runs a fluid processing procedure on the fluid processing system 10, the operator interacts with a user interface 98, which may include a screen, a keyboard, touchscreen, buttons, print-out, voice input/output, or any suitable interface. At each step of the procedure, orchestrated by a processing circuit within system 10, the interface 98 may prompt the human operator to execute one or more actions as part of the step. Such actions may include fitting one or more cassettes 16 into cassette holder 94, connecting a tubing 30 to a solution container 20, opening or closing off a tubing connection, accessing a blood source, etc. The failsafe feature may be incorporated into this series of steps as an authentication step that allows the fluid processing system 10 to recognize and approve or disapprove a particular medical solution for the particular step of the procedure.

Figure 4:
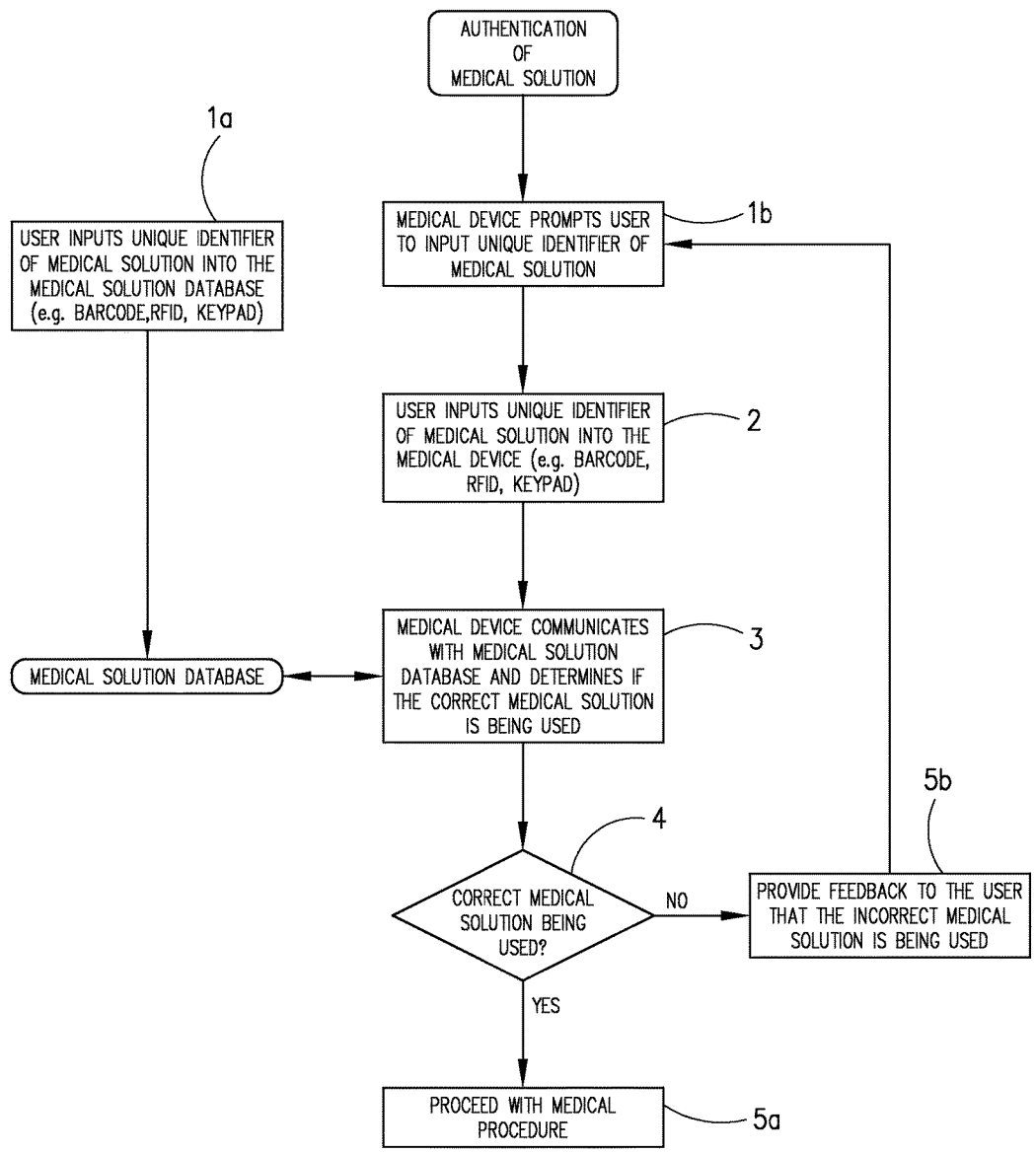
FIG. 4 is flow diagram of a series of prompts and/or steps displayed in the course of authenticating a medical solution, according to an exemplary embodiment.

FIG. 4 illustrates an exemplary methodology operable by a processing circuit of the fluid processing system 10 to provide one or a series of prompts to a human operator in the course of authenticating a medical solution or otherwise operating system 10. At step 1*a*, a user or technician inputs unique identifier information for one or more medical solution into a medical solution database using a suitable input device (e.g., barcode, active or passive RFID, keypad, touchscreen, etc.). The database information can be used to classify and categorize the types of solutions that are compatible with different types of procedures (e.g., what are authorized and what are not authorized depending on different procedure types). At step 1*b*, the user interface 98 prompts the operator to input a unique identifier of the medical solution container used in a fluid processing procedure for the system to authenticate. At step 2, the user inputs the unique identifier of the medical solution into the medical device. As shown in FIG. 3, the unique identifier may include one or more of the manufacturer name 51, solution name 52, solution contents 53, content details 54, product code 55, a bar code 56, an active or passive RFID tag 57, a photo-recognizable image, or other identifier. In the case of a bar code 56, active or passive RFID tag 57, or a photo-recognizable image, the system 10 may be equipped with a scanner that scans and recognizes the bar code 56 or tag 57. At step 3, the system 10 communicates with the medical solution database (e.g., over a network, Wi-Fi, serial cable, etc.) and determines if the correct medical solution is being used for the particular procedure. At step 4, if the solution is an accepted or authorized solution for the particular procedure, the process moves to step 5*a* and the medical procedure may proceed. However, if the solution is not an accepted or authorized solution for the particular procedure, the process moves to step 5*b* where the user is provided feedback that the incorrect medical solution is being used and/or inputted and the process returns to step 1*b* so that the user can input the same solution again or try inputting information for a different solution. In the event that the inputted medical solution is actually a correct solution but is not contained in the database, the corrective action may include the operator simply scanning or manually entering the new medical solution's unique identifiers into the database and configuring the solution as an approved, listed, or recognized solution by storing the identifier or identifiers in a list in the database, as shown in step 1*a*.

Each time a solution container 20 is to be connected to the system 10, the human operator may be prompted to follow one or more stages of these authentication procedures. These features may be implemented across different manufacturers and product lines. In the event that the solution is not approved by the system 10, the user may be prompted in step 5*b* using a number of different methods, including for example, an alarm, a prompt for the user to re-enter, a lock on the machine to prevent further use, a prompt for the user to enter the identifier, perhaps with an approval code from a manager, a termination of the procedure, a suspension of the procedure, a suspension of activity until the user corrects the error, etc. In the event that the solution is approved by the system in step 5*a*, the system 10 may, for example, provide a positive alert to the user, move to the next step of the procedure, increment a record of the number of times this container has been used on the system, etc.

According to an exemplary embodiment, the methodology shown in FIG. 4 may be implemented by a processing circuit of the system 10 illustrated in FIG. 1 in the course of a procedure such as a plasma exchange procedure. At a step in which the plasma exchange procedure requires connecting to an anticoagulant solution, the user interface 98 may prompt the operator to input a unique identifier of the anticoagulant container for the system 10 to authenticate, as shown in step 1*b*. The unique identifier the operator elects to input may be a manufacturer name 51 and product code 55, although it may be any other identifier. Following the input of the manufacturer name 51 and product code 55 of the anticoagulant solution container at step 2, the system 10 may source information from an online or offline database of medical solutions, as indicated in step 3. If the anticoagulant solution is within a category of accepted solutions for the anticoagulant step of the procedure, as determined by the information from the database, the system 10 is configured to approve the anticoagulant solution and/or proceed to drawing the anticoagulant solution into the fluid circuit 12 at step 5*a*. However, if the anticoagulant solution is not within a category of accepted anticoagulant solutions for the step in the procedure, the system 10 may prompt the user, e.g., with the sound of an alarm, that an unapproved or unlisted or unrecognized solution has been inputted and will not proceed to the next step of the procedure until corrective action has been taken, as shown in step 5*b*. In the event that the inputted medical solution is actually a correct anticoagulant solution but is not contained in the database, the corrective action may include the operator simply scanning or manually entering the new anticoagulant solution's unique identifiers into the database and configuring the solution as an approved, listed, or recognized anticoagulant solution by storing the identifier or identifiers in a list in the database, as shown in step 1*a*. In the event that the inputted medical solution is actually an incorrect anticoagulant solution or not an anticoagulant solution at all, the operator will be placed on notice of the mistake and will take corrective action by returning to step 1*b* and choosing a correct anticoagulant solution.

The processing circuit of system 10 may comprise one or more analog and/or digital electronic components, such as a microprocessor, microcontroller, application-specific integrated circuit, programmable logic, etc., configured to carry out one or more of the steps described herein. The processing circuit may be programmed with an algorithm stored in a memory device configured to cause the processing circuit to carry out the steps. System 10 may further comprise a network interface circuit configured to communicate over a network (e.g., a wired or wireless network, an Ethernet, a local area network, a wide area network, a personal area network, an IEEE 802.11x network, etc.). The network interface circuit may comprise analog and/or digital components configured for communication.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A system for authenticating a medical solution during a biological fluid processing procedure, the system comprising:

a biological fluid processing device, comprising a first pump, a user interface, and a separator, configured to convey a source biological component from an inlet of the separator for separation into a first component and a second component;

a fluid circuit configured to associate with the biological processing device, wherein the fluid circuit comprises:

a first container containing a first fluid comprising at least one of an infusion solution, blood additive solution, anticoagulant solution, saline solution, blood component solution, and replacement fluid, for combination with the source biological component, the first component, and/or the second component during a first step of the fluid processing procedure;

a second container containing a second fluid comprising at least one of an infusion solution, blood additive solution, anticoagulant solution, saline solution, blood component solution, and replacement fluid, for combination with the source biological component, the first component, and/or the second component during a second step of the fluid processing procedure;

a plurality of fluid pathways connecting the separator, the first container, and the second container, wherein fluid flow is actuated through the plurality of fluid pathways by the pump;

a microprocessor controller in communication with the user interface of the biological fluid processing device and configured for communication with a local and/or remote database of approved medical solution identifiers, wherein the biological processing device is configured to process in the first step the first fluid from the first container having at least one identifier and to process in the second step the second fluid from the second container having at least one identifier;

wherein the microprocessor controller is programmed with a first set of identifiers approved for the first step and a second set of identifiers approved for the second step;

wherein the microprocessor controller is configured to:

display a prompt to a user via the user interface at the first step to input a first identifier from the first container having at least one identifier;

compare the first identifier to the first set of identifiers;

proceed with the first step only if the first identifier is a match with any identifier within the first set, wherein the first step comprises flowing the first fluid from the first container via the first pump and combining the first fluid with the source biological component, the first component, and/or the second component;

display a prompt to a user via the user interface at the second step to input a second identifier from the second container having at least one identifier;

compare the second identifier to the second set of identifiers; and proceed with the second step only if the second identifier is a match with any identifier within the second set, wherein the second step comprises flowing the second fluid from the second container via the first pump or a second pump and combining the second fluid with the source biological component, the first component, and/or the second component.

2. The system of claim 1, wherein the microprocessor controller is further configured to trigger an alert via the user interface if the first identifier is not a match with any identifier within the first set or if the second identifier is not a match with any identifier within the second set.

3. The system of claim 1, wherein the first fluid and/or the second fluid comprises at least one of an infusion solution, blood additive solution, anticoagulant solution, saline solution, blood component solution, and replacement fluid.

4. The system of claim 1, wherein the first set and/or the second set of identifiers comprises identifiers associated with at least one of a manufacturer name, solution name, solution contents, content details, product code, bar code, and active or passive RFID tag.

5. The system of claim 1, wherein the biological fluid processing device further comprises a memory within which the database is disposed and wherein the database is configured to be updated over a network.

6. The system of claim 1, wherein the microprocessor controller is configured to read the first identifier or the second identifier via at least one of a data card, a radio frequency identifier, a bar code, a personal digital assistant, a mobile phone, and a disk-based medium.

7. The system of claim 1, wherein the biological fluid processing device further comprises a memory within which the database of approved medical solution identifiers is located.

8. The system of claim 1, wherein the user interface includes at least one of a screen, keyboard, touchscreen, buttons, print-out, voice input, and voice output.

9. The system of claim 1, wherein the biological fluid processing device is configured to communicate with the database of approved medical solution identifiers over a network.

10. A method of authenticating a medical solution during a biological fluid processing procedure, the method comprising:

providing a biological fluid processing device, comprising a first pump, a user interface, and a separator, configured to convey a source biological component from an inlet of the separator for separation into a first component and a second component;

providing a fluid circuit configured to associate with the biological processing device, wherein the fluid circuit comprises 1) a first container containing a first fluid, 2) a second container containing a second fluid, and 3) a plurality of fluid pathways connecting the separator, the first container, and the second container, wherein fluid flow is actuated through the plurality of fluid pathways by the first pump;

providing a microprocessor controller in communication with the user interface of the biological fluid processing device and configured for communication with a local and/or remote database of approved medical solution identifiers, wherein the biological processing device is configured to process in a first step the first fluid from the first container having at least one identifier and to process in a second step the second fluid from the second container having at least one identifier requesting at the first step of the biological fluid processing procedure via the microprocessor controller and the user interface a first identifier from the first container;

receiving via the user interface the first identifier from the first container;

comparing via the microprocessor controller the first identifier from the first container and a first set of approved identifiers for the first step programmed for the microprocessor controller;

performing the first step only if the first identifier from the first container is a match with any of the first set of approved identifiers for the first step, wherein the first step comprises flowing the first fluid from the first container via the first pump and combining the first fluid with the source biological component, the first component, and/or the second component;

requesting at the second step of the biological fluid processing procedure via the microprocessor controller and the user interface a second identifier from the second container;

receiving via the user interface the second identifier from the second container;

comparing via the microprocessor controller the second identifier from the second container and a second set of approved identifiers for the second step programmed for the microprocessor controller; and performing the second step only if the second identifier from the second container is a match with any of the second set of approved identifiers for the second step, wherein the second step comprises flowing the second fluid from the second container via the first pump or a second pump and combining the second fluid with the source biological component, the first component, and/or the second component.

11. The method of claim 10, further comprising alerting the user via the user interface if the first identifier is not a match with any of the first set of approved identifiers for the first step.

12. The method of claim 10, wherein the first fluid and/or the second fluid comprises at least one of an infusion solution, blood additive solution, anticoagulant solution, saline solution, blood component solution, and replacement fluid.

13. The method of claim 10, wherein the first set and/or the second set of identifiers comprises identifiers associated with at least one of a manufacturer name, solution name, solution contents, content details, product code, bar code, and active or passive RFID tag.

14. The method of claim 10, wherein the biological fluid processing device further comprises a memory within which the database is disposed, wherein and the database is configured to be updated over a network.

15. The method of claim 10, wherein the microprocessor controller is configured to read the first identifier or the second identifier via at least one of a data card, a radio frequency identifier, a bar code, a personal digital assistant, a mobile phone, and a disk-based medium.

16. The method of claim 10, wherein the microprocessor controller is configured to communicate with the database of approved medical solution identifiers stored within a memory of the biological fluid processing device.

17. The method of claim 10, wherein the user interface includes at least one of a screen, keyboard, touchscreen, buttons, print-out, voice input, and voice output.

18. The method of claim 10, wherein the biological fluid processing device is configured to communicate with the database of approved medical solution identifiers over a network.

19. A system for authenticating a medical solution during a biological fluid processing procedure, the system comprising:

a biological fluid processing device, comprising a first pump, a user interface, and a separator, configured to convey a source biological component from an inlet of the separator for separation into a first component and a second component;

a fluid circuit configured to associate with the biological processing device, wherein the fluid circuit comprises:
a first container containing a first fluid for combination with the source biological component, the first component, and/or the second component during a first step of the fluid processing procedure;
a second container containing a second fluid for combination with the source biological component, the first component, and/or the second component during a second step of the fluid processing procedure;
a plurality of fluid pathways connecting the separator, the first container, and the second container, wherein fluid flow is actuated through the plurality of fluid pathways by the pump;

a microprocessor controller in communication with the user interface of the biological fluid processing device and configured for communication with a local and/or remote database of approved medical solution identifiers, wherein the biological processing device is configured to process in the first step the first fluid from the first container having at least one identifier and to process in the second step the second fluid from the second container having at least one identifier;

wherein the microprocessor controller is programmed with a first set of identifiers approved for the first step and a second set of identifiers approved for the second step;

wherein the microprocessor controller is configured to:
receive at the first step a first identifier of the first container having at least one identifier;
compare the first identifier of the first container to the first set of identifiers approved for the first step;
proceed with the biological fluid procedure only if the first identifier of the first container is a match with any identifier within the first set of identifiers approved for the first step, wherein the biological fluid procedure comprises flowing the first fluid from the first container via the first pump and combining the first fluid with the source biological component, the first component, and/or the second component;
receive at the second step a second identifier of the second container having at least one identifier;
compare the second identifier of the second container to the second set of identifiers approved for the second step; and
proceed with the biological fluid procedure only if the second identifier of the second container is a match with any identifier within the second set of identifiers approved for the second step, wherein the biological fluid procedure comprises flowing the second fluid from the second container via the first pump or a second pump and combining the second fluid with the source biological component, the first component, and/or the second component.

20. The biological fluid processing system of claim 19, wherein the microprocessor controller is configured to communicate with the database of approved medical solution identifiers located in a memory remote from the biological fluid processing device over a network interface device.

21. The biological fluid processing system of claim 19, wherein the biological fluid processing system comprises an apheresis system.

* * * * *